United States Patent [19]

Hazen et al.

[11] Patent Number: 4,834,908
[45] Date of Patent: May 30, 1989

[54] ANTAGONISM DEFEATING CROP OIL CONCENTRATES

[75] Inventors: James L. Hazen, Apex; Rudolf H. A. Frank; Paul S. Zorner, both of Durham, all of N.C.; James R. Campbell, Budd Lake, N.J.

[73] Assignee: BASF Corporation, Parsippany, N.J.

[21] Appl. No.: 104,658

[22] Filed: Oct. 5, 1987

[51] Int. Cl.$^4$ .................. B01J 17/44; B01J 17/34
[52] U.S. Cl. ................... 252/356; 71/DIG. 1; 106/250; 106/267; 252/351; 252/354
[58] Field of Search ............... 106/250, 267; 71/DIG. 1, 106, 127; 252/356; 260/398

[56] References Cited

U.S. PATENT DOCUMENTS

| | | | |
|---|---|---|---|
| 3,990,884 | 11/1976 | Barker | 71/DIG. 1 |
| 3,997,322 | 12/1976 | Ratledge | 71/DIG. 1 |
| 4,313,847 | 2/1982 | Chasin et al. | 252/356 |
| 4,447,257 | 5/1984 | Gerwick, III | 71/DIG. 1 |
| 4,608,202 | 8/1986 | Lepper et al. | 260/410.9 R |

FOREIGN PATENT DOCUMENTS 0027802  2/1984  Japan .................... 71/106

OTHER PUBLICATIONS

Hawley, G., "The Condensed Chemical Dictionary", Tenth Edition, p. 450.

Primary Examiner—Richard L. Raymond
Assistant Examiner—Susan P. Treanor
Attorney, Agent, or Firm—William G. Conger

[57] ABSTRACT

Crop oil concentrates are disclosed which not only increase the herbicidal efficacy of herbicides from diverse chemical classes, but moreover assist in defeating the apparent antagonism which often arises when two or more herbicides are utilized together.

34 Claims, No Drawings

ANTAGONISM DEFEATING CROP OIL CONCENTRATES

BACKGROUND OF THE INVENTION

1. Field of the Invention

The subject invention relates to crop oil concentrates. More particularly, the subject invention relates to improved crop oil concentrates which enhance the efficacy of herbicides, and which defeat the antagonism which often results when two or more herbicides are used in combination.

2. Description of the Related Art

It is well established that a variety of adjuvants play important roles in the application of herbicides. These adjuvants are a diverse group of components with equally diverse functions which may often be determined from their generic names, i.e. "spreaders," "stickers," "solubilizers," "emulsifiers," "flow control agents," "drift control agents," and so on. Among the many useful herbicide adjuvants are the so-called "crop oil concentrates."

Crop oil concentrates are often recommended by herbicide manufacturers and formulators for inclusion in tank mixes to increase the efficacy of postemergent herbicide formulations. Crop oil concentrates are available from a variety of sources, and generally consist of from 75-95 percent by weight of a hydrocarbon oil or solvent with the balance being a surfactant. The hydrocarbons which form the bulk of the crop oil concentrate may be derived from mineral (petroleum) or vegetable sources. For example, U.S. Pat. No. 3,990,884 discloses an herbicide system containing, in addition to the 4-chloro-2-butynyl-m-chlorocarbanilate active ingredient, from 10-30% by weight of an oxyethylated fatty alcohol, 5-15% of calcium dodecylbenzene sulfonate and 25 to 75% of a hydrocarbon oil.

Although the use of selected crop oil concentrates may enhance herbicidal efficacy, it is well known that many of the proprietary concentrates available are not as effective as others. Some may even impact negatively upon herbicidal efficacy. Additionally, there is a great deal of inconsistency with regard to the make up of available crop oil concentrates. Finally, to further complicate the situation, manufacturers frequently change the formulations without notifying the consumer, resulting in a great deal of uncertainty with regard to their performance.

In recent years, the situation with respect to crop oil concentrates has achieved such a level of notoriety that some agriculturists refer to them as "snake oils." Thus there is a need in the agricultural sector, for a crop oil concentrate with a well defined make-up which is capable of enhancing the efficacy of a broad spectrum of herbicides, and which gives reproducible results.

SUMMARY OF THE INVENTION

It has now been surprisingly discovered that certain crop oil concentrates enhance activity of a broad spectrum of herbicides to an unexpectedly high level, and moreover these same crop oil concentrates surprisingly defeat the antagonism which is often created when two or more herbicides are utilized simultaneously.

DESCRIPTION OF THE PREFERRED EMBODIMENTS

The crop oil concentrates of the subject invention comprise a mixture of (a) a lower alkanol ester of a long chain carboxylic acid; (b) an anionic surfactant derived from esterification of a polyoxyalkylene nonionic surfactant with a dihydric or trihydric inorganic acid or by carboxylation with an organic acid derivative; (c) a long chain carboxylic acid; and (d) a hydrocarbon component.

The lower alkanol ester of the long chain carboxylic acid (a) may be considered as derived from a lower alkanol having from 1 to 4 carbon atoms, such as methyl alcohol, ethyl alcohol, propyl alcohol, or butyl alcohol, and a long chain carboxylic acid. The methyl and ethyl esters are preferred. Most particularly, the methyl esters are utilized. The long chain carboxylic acid generally contains from 10-20 carbon atoms, preferably from 14-18 carbon atoms. Preferred are those carboxylic acids obtainable from natural sources such as fats and oils, for example lauric, myristic, stearic, linoleic, linolenic, palmitic, and oleic acids. Mixtures of these acids are also useful. Preferred are oleic and palmitic acids and their mixtures. Thus the most preferred alkanol esters are methyl oleate, methyl palmitate, and mixtures of these esters. In the remainder of the specification, such compounds will be referred to as lower alkanol esters.

The anionic surfactants (b) which are useful in the practice of the subject invention are preferably the partial sulfate and phosphate esters of polyoxyalkylene ethers. These partial esters are prepared by methods well known to those skilled in the art, for example by reacting one of the well known and commercially available monohydric polyoxyalkylene ethers with sulfuric acid or phosphoric acid or their chemical equivalents. The sulfate esters so obtained consist predominately of the half ester (monoester) while the phosphate esters generally contain both mono- and diesters. Also useful, are the carboxylate surfactants.

The methods of preparation of such surfactants are well known to those skilled in the art. The sulfate esters may be prepared, for example, by reacting a suitable monofunctional polyoxyalkylene ether with sulfuric acid or its chemical equivalent, preferably sulfamic acid or sulfur trioxide. The phosphate esters may be prepared similarly by reaction of the monofunctional polyoxyalkylene ether with phosphoric acid, diphosphorus pentoxide, polyphosphoric acid, or phosphorus oxytrichloride. Methods of preparation are described in the treatise *Nonionic Surfactants*, Martin Schick, Ed., Marcel Dekker, New York, ©1967, in Chapter 11, pp 372-394.

The nonionic, monofunctional polyoxyalkylene ethers used to prepare the sulfate and phosphate esters are also well known to those skilled in the art, and are available commercially from many sources. Preferred nonionic, monofunctional polyoxyalkylene ethers have molecular weights of from about 400 to about 3000 Daltons, more preferably from about 600 to about 1200 Daltons, and particularly about 800 Daltons.

The preferred polyethers are prepared by oxyalkylating a monofunctional initiator by known methods. Preferred initiators are the alkylphenols such as octyl- and nonylphenol, and the aliphatic alcohols, particularly the latter. The preferred aliphatic alcohols have from 6 to 30, more preferably from 10 to 20, and in particular, from 12 to 16 carbon atoms in the aliphatic residue.

The alkylene oxides which may be used to prepare the nonionic monofunctional polyoxyalkylene intermediates include ethylene oxide, propylene oxide, and butylene oxide. Tetrahydrofuran may also be useful.

Preferred alkylene oxides are ethylene oxide and propylene oxide. When both these oxides are utilized, they may be added simultaneously, in sequence, or in combinations of these modes of addition, to prepare block, heteric, and blockheteric surfactants. Ethylene oxide may also be used alone to form homopolymeric polyoxyethylene polyethers.

The carboxylate surfactants are derived from oxyethylated alipatic alcohols by reaction with chloroacetic acid in the presence of base. The preparation is described in the Schick treatise, supra, at pages 388–89. Preferably, the aliphatic alcohol contains from 8 to 18, more preferably from 10 to 14 carbon atoms, and is oxyethylated with from 2 to 10, preferably from 3 to 8 moles of ethylene oxide. Preferred is the carboxylate formed from the reaction of chloroacetic acid and the four mole oxyethylate of lauryl alcohol. Reference in the specification and the claims to "carboxylates" of monohydroxyl functional polyoxyalkylene ethers is to this type of surfactant.

The long chain carboxylic acid (c) may have a chain length, of from 10 to 20 carbon atoms. Preferably, the carboxylic acid is selected from the group of naturally occurring fatty acids such as stearic acid, linoleic acid, linolenic acid, palmitic acid, oleic acid, and the like and mixtures thereof. The unsaturated fatty acids are preferred. Most preferably, the organic acid is oleic acid. The long chain carboxylic acid may be added as an individual component, or it may be derived from the in situ hydrolysis of the lower alkanol ester (a). It is preferable to add the long chain carboxylic acid as an individual component and thus substantially avoid changes in the overall composition over time due to ester hydrolysis.

Components (a), (b), and (c) may be used alone as the crop oil concentrate. However, in such a case, the viscosity of the concentrate is higher than is desirable. Furthermore, at low temperatures, certain of the components of the concentrate may precipitate to some degree. Such low temperatures are often encountered in the northernly climates or in the early spring. Hence it is desirable that component (d), the hydrocarbon component, be added to decrease the viscosity of the concentrate and to help prevent component separation at low temperatures.

The hydrocarbon component (d) may be derived principally from vegetable or petroleum sources. Preferred are the aromatic solvents particularly those containing alkylated benzenes and naphthalenes. Such solvents are readily available from a number of sources, for example, the Shellsolve ® solvents available from the Shell Oil Co., Houston, Tex., and the Aromatic ® 150 and 200 solvents available from the Exxon Corporation. The hydrocarbon component may also contain up to about 30 percent by weight, preferrably from 10–30 percent by weight of a solvent soluble alcohol, for example isooctanol, to maintain or enchance the physical properties of the blend. Other solvent soluble alcohols which are suitable are those which generally contain from 5 to about 18 carbon atoms, preferably from 5 to about 10 carbon atoms. The term "hydrocarbon component" as used herein should be taken as including both aliphatic and aromatic solvents as well as their mixtures, including also the solvent soluble alcohol component described immediately above. The hydrocarbon component is believed to exert some biochemical effect in concert with that of the remaining ingredients, and hence may be considered an active ingredient.

When utilized as a crop oil concentrate without the hydrocarbon component, the composition generally contains, in percent by weight relative to the total weight of the concentrate, from 20 to 90 percent lower alkanol ester, 4 to 40 percent anionic surfactant, and 2 to 20 percent fatty acid. Preferably, the composition contains 30 to 80 percent lower alkanol ester, 4 to 20 percent surfactant, and 4 to 16 percent fatty acid. Most preferably it contains 70 to 80 percent lower alkanol ester, 10 to 20 percent surfactant, and 8 to 14 percent fatty acid.

The prefered hydrocarbon component-containing crop oil concentrates generally contain, in percent by weight relative to the total weight of the crop oil concentrate, from about 10 to about 60 percent of lower alkanol ester, from about 2 to about 20 percent anionic surfactant, from 1 to about 10 percent fatty acid, and from 70 to about 30 percent hydrocarbon component. More preferably, the crop oil concentrate contains from 25 to 45 percent lower alkanol ester, 2 to about 10 percent anionic surfactant, 2 to 8 percent fatty acid, and 60 to 40 percent hydrocarbon component. Most preferably, the crop oil concentrate contains from about 35 to about 40 percent lower alkanol ester, from about 5 to about 10 percent anionic surfactant, from about 4 to 7 percent fatty acid, and about 50 percent hydrocarbon component. The hydrocarbon component may optionally contain up to about 30 percent, preferably from 10 to about 20 percent, and most preferably about 18 percent of a solvent soluble alcohol.

The crop oil concentrates of the subject invention may be utilized in many postemergent herbicide formulations, generally in amounts of from about 0.5 to about 8 l/ha, preferably from about 2 to about 5 l/ha. Many manufacturers recommend the use of crop oil concentrates for particular applications or, in some cases, for all applications of their herbicides. In other cases, the concentrates may be used as experience dictates. The crop oil concentrates of the subject invention have been found effective with herbicides of diverse chemical structure, for example with the cyclohexenone herbicides, with benzothiadiazinonedioxide herbicides, with diphenylether herbicides, with dipyridilium herbicides and with aryloxyphenoxy herbicides including analogues containing heterocycles such as the quinoxalinyloxyphenoxy herbicides. The crop oil concentrates are especially effective with the cyclohexenone-type herbicides, and particularly when these herbicides are used in conjunction with herbicides of other classes.

The cyclohexenone herbicides with which the subject invention crop oil concentrates may be used are well known. Examples of their preparation and use may be found in U.S. Pat. Nos. 3,950,420; 4,011,256, 4,249,937, and 4,666,510. Specific mention may be made of certain of the more common cyclohexenones, including alloxydim, sethoxydim, cycloxydim, clethodim, and cloproxydim.

The diphenyl ether herbicides and their analogues are likewise well known. These herbicides are described, for example, in chapter 14 of *Herbicides*, P. C. Kearney et. al., published by Marcel Dekker, Inc., New York ©1976. Many other classes of herbicides are also described in this two volume treatise. Also well known are the dipyridilium herbicides such as paraquat, diquat, and morfamquat.

In the examples which follow, herbicides or herbicide mixtures are tested for their efficacy against a variety of common weeds. In many cases, comparisons are made to similar compositions containing other crop oil concentrates. The "standard" crop oil concentrate used for comparison purposes is "Booster Plus E," a product of the Agway Corporation. This product has been widely used in herbicide applications and appears to have consistent formulation and product quality. In the examples, this "standard" crop oil concentrate is labeled "OC". In certain cases, sunflower oil methyl ester, nonionic surfactants, or other crop oils are compared to the subject invention crop oil concentrates. In all the tables showing efficacy of the crop oil concentrate/herbicide mixtures against various species of weeds, the numerical values in the tables represent the percentage of weed control, or percent kill of the various species. The term "Concentrate" is used to represent "crop oil concentrate" in these tables.

EXAMPLES 1-3

Crop oil concentrates COC-1, COC-2, and COC-3 were prepared by mixing together the following ingredients in parts by weight:

|  | COC-1 | COC-2 | COC-3 |
| --- | --- | --- | --- |
| C-65 ® methylester[1] | 37.5 | 37.5 | 30.0 |
| Klearfac ® AA270 anionic surfactant[2] | 7.5 | 7.5 | 15.0 |
| Oleic acid | 5.0 | 5.0 | 5.0 |
| Aromatic ® 150 solvent[3] | 50.0 | 42.5 | 35.0 |
| Isooctanol | — | 7.5 | 15.0 |
|  | 100.0 | 100.0 | 100.0 |

[1]C-65 ® methylester is a product available from the Stepan Chemical Co. It is an approximately 1:1 blend of methyloleate and methylpalmitate derived from natural sources.
[2]Klearfac ® AA270 is a phosphate ester surfactant derived from a nonionic polyether having a molecular weight of about 800 Dalton. It is available from BASF Corp., Parsippany, N.J.
[3]Aromatic ® 150 solvent is a mixed aromatic solvent available from the Exxon Chemical Corporation.

In comparing the efficacy of the subject invention crop oil concentrates with alternative crop oil concentrates, the respective concentrates were added at levels of generally from 2 to 5 l/ha to tank mixes of the herbicides and agitated to prepare a uniform mixture. Cyclohexenone herbicides A, B, C, and D are experimental cyclohexenones of the type disclosed in U.S. Pat. Nos. 4,249,937, 4,011,256, and 3,950,420.

Standard abbreviations for the various weed species found in the text which follows may be found below:

| AVEFA | Avena fatua | wild oats |
| --- | --- | --- |
| AVESA | Avena sativa | oats (volunteer) |
| BRAPP | Brachiaria platyphylla | broadleaf signal grass |
| BROSE | Bromus secalinus | ryebrome |
| CHEAL | Chenopodium album | fat hen |
| DAOTE | Daubentonia texana | coffee weed |
| DATST | Datura stramonium | thorn-apple |
| DIGSA | Digitoria sanguinalis | large crabgrass |
| ECHCG | Echinochloa crus-galli | barnyard grass |
| FESAR | Festuca arundinacea | tall fescue |
| HORVU | Hordeum vulgare | barley (volunteer) |
| IPOLA | Ipomoea lacunosa | pitted morning glory |
| LEFTI | Leptochloa filiformis | red sprangletop |
| LOLMU | Lolium multiflorum | annual ryegrass |
| PANTE | Panicum texanum | witchgrass |
| POAAN | Poa annua | meadow grass |
| POAPR | Poa pratensus | smooth meadow grass |
| SETFA | Setaria faberii | giant fox tail |
| SETLU | Setaria lutescens | yellow foxtail |
| SETVI | Setaria viridis | green foxtail |
| SORHA | Sorghum halepense | Johnson grass |
| TRZAX | Triticum aestivum | wheat (volunteer) |
| XANPE | Xanthium pennsylvanicum | cocklebur |
| ZEAMX | Zea mays | corn (volunteer) |

Herbicide mixtures are frequently used in weed control. Often, one selective herbicide will show great efficacy in controlling several weed species but will have little effect on others. When complete weed control is desired either sequential application of two or more herbicides is required or one application of a mixture of two or more herbicides is required. Successive herbicide application is not cost-effective. However, the use of mixtures of herbicides often fails to achieve the desired results due to apparent antagonism between the herbicides.

Antagonism may be true biological antagonism where, for example, the biochemical effect of one herbicide is partially or wholly destroyed by the second herbicide. Antagonism may also be physical antagonism where either one herbicide or its formulation ingredients wholly or partially prevents the biological uptake of the second herbicide. It is frequently difficult, if not impossible, for the agriculturist to identify which of these types of antagonism is operative. Thus the term "apparent antagonism" is an appropriate one to describe the net, observable effect—a decrease in the efficacy of one herbicide when used in conjunction with another.

An example of apparent antagonism frequently occurs when grass herbicides and broadleaf herbicides are used simultaneously. Cyclohexenone herbicide A for example, is very effective in controlling a number of obnoxious grass species in various crops. Cyclohexenone A has little or no effect, however, on broadleaf weeds, where bentazon is very effective. When cyclohexenone A is used with the "standard" crop oil concentrate, control of POAAN and BROSE is greater than 90 percent control, a very acceptable value. There is no grass control at all in the presence of bentazon when the "standard" oil concentrate is used. When the crop oil concentrate of the subject invention is used, however, control is maintained at high levels. These results are summarized in Table I.

TABLE I

Effect of Oil Concentrates on Antagonism Between Cyclohexenone A and Bentazon

| Herbicide @ rate | Oil Concentrate @ rate | Species: | | | | | |
| --- | --- | --- | --- | --- | --- | --- | --- |
|  |  | POAAN | FESAR | POAPR | BROSE | AVESA | OVERALL |
| Cyclohexenone A @ 75 g/ha | OC @ 2 l/ha | 91 | 95 | 97 | 91 | 99 | 92 |
|  | COC-1 @ 2 l/ha | 95 | 96 | 99 | 92 | 99 | 96 |
| Cyclohexenone A @ 75 g/ha + bentazon @ 70 g/ha | OC @ 2 l/ha | 0 | 94 | 96 | 0 | 94 | 40 |
|  | COC-1 @ 2 l/ha | 89 | 95 | 98 | 93 | 97 | 91 |

When normal rates of either sethoxydim or cycloxydim are used in conjunction with bentazon, control of several week species, may be adversely effected. In Table II, sethoxydim is shown to be very effective on all weed species tested when used with the standard oil concentrate or with a commercially available nonionic surfactant, e.g. PLURAFAC ® LF700 nonionic surfactant. However when bentazon, (Basagran ® herbicide) is added, the control of all grass species decreases. TRZAX and HORVU control reaches totally unacceptable levels. Replacement of the oil concentrate or nonionic surfactant with the crop oil concentrate of the subject invention results in raising the level of control to substantially the same level as sethoxydim when used without bentazon.

TABLE II

Effect of Oil Concentrates on Herbicide Antagonism

| Herbicide @ rate | Concentrate (@ 2 l/ha) | Species: TRZAX | AVESA | LOLMU | HORVU | OVERALL |
|---|---|---|---|---|---|---|
| Sethoxydim @ 200 g/ha | OC | 90 | 98 | 97 | 83 | 88 |
|  | LF-700 | 93 | 99 | 98 | 84 | 90 |
|  | COC-1 | 94 | 99 | 99 | 85 | 90 |
| Sethoxydim @ 200 g/ha + bentazon @ 720 g/ha | OC | 32 | 93 | 90 | 28 | 50 |
|  | LF-700 | 20 | 77 | 72 | 23 | 40 |
|  | COC-1 | 80 | 98 | 94 | 72 | 80 |

[1]PLURAFAC LF-700 nonionic surfactant, a product of BASF Corporation, Parsippany, N.J.

As a further example, the addition of bentazon to tank mixes of cycloxydim and standard crop oil concentrate lowers overall weed control from 78 percent control, a quite acceptable level, to only 32 percent control, a level which is unacceptable. As Table IIa demonstrates, the use of COC-3 in place of the standard concentrate raises control to 73 percent. Thus the crop oil concentrate of the subject invention once again defeats the apparent antagonism displayed by the mix.

Not only are the crop oil concentrates efficient in defeating herbicide antagonism, they are valuable as highly effective crop oil concentrates in tank mixes containing but a single herbicide. The tables which follow illustrate the greater efficacy of the subject invention crop oil concentrates as compared to other concentrates.

TABLE IIa

Effect of Oil Concentrate on Cycloxydim/Bentazon Antagonism in Grass Control

| Herbicide | Oil Concentrate @ 1.5 l/ha | Species: DIGSA | ECHCG | ZEAMX | OVERALL |
|---|---|---|---|---|---|
| cycloxydim @ 50 g/ha | OC | 94 | 98 | 23 | 78 |
|  | COC-3 | 96 | 98 | 76 | 92 |
| cycloxydim @ 50 g/ha + bentazon @ 720 g/ha | OC | 40 | 40 | 10 | 32 |
|  | COC-3 | 86 | 92 | 23 | 73 |

TABLE III

Grass Control by Cycloxydim at 100 g/ha

| Conven-rate* | Species TRZAK | AVESA | LOLMU | HORVU | OVER-ALL |
|---|---|---|---|---|---|
| OC | 73 | 100 | 99 | 91 | 90 |
| COC-1 | 82 | 100 | 99 | 96 | 93 |
| COC-2 | 87 | 100 | 99 | 98 | 96 |

*at 1.5 l/ha

TABLE IV

Grass Control By Sethoxydim at 150 g/ha

| Concen-trate* | Species TRZAX | AVESA | LOLMU | HORVU | OVER-ALL |
|---|---|---|---|---|---|
| OC | 30 | 92 | 86 | 30 | 62 |
| COC-1 | 73 | 99 | 98 | 68 | 85 |
| COC-2 | 75 | 99 | 98 | 77 | 87 |

*at 2.0 l/ha

TABLE V

Grass Control By Sethoxydim at 125 g/ha

| Concen-trate* | Species TRZAX | AVESA | LOLMU | HORVU | OVER-ALL |
|---|---|---|---|---|---|
| OC | 77 | 99 | 99 | 65 | 79 |
| COC-1 | 90 | 99 | 99 | 86 | 92 |
| COC-2 | 89 | 95 | 99 | 84 | 92 |
| Sunflower oil methyl esters | 85 | 99 | 99 | 80 | 87 |

*at 2.0 l/ha

Tables III–V indicate that the crop oil concentrates of the subject invention are more effective than either the "standard" concentrate or sunflower oil methyl ester in achieving effective control of the grass species tested. This is particularly evident with regard to control of TRZAX (volunteer wheat). As certain grass species are more sensitive than others, the herbicide application rate would have to adjusted for each species to permit demonstration of the greater efficacy of the subject invention crop oil concentrates for each individual weed species.

A major feature of the crop oil concentrates of the subject invention is that they allow retention of high levels of control while using less herbicide, thus decreasing costs and benefiting the environment. This is demonstrated in Table VI.

TABLE VI

Effect of Oil Concentrate on Efficacy of Sethoxydim Across Species[1]

| SPECIES | Oil Concentrate[2] | Sethoxydim Rate (g/ha) 7.0 | 3.5 | 1.7 | 0.8 |
|---|---|---|---|---|---|
| SETFA | OC | 100 | 30 | 0 | 0 |
|  | COC-1 | 100 | 100 | 95 | 40 |
| DIGSA | OC | 50 | 20 | 0 | 0 |
|  | COC-1 | 98 | 50 | 30 | 0 |
| BRAPP | OC | 100 | 100 | 30 | 0 |
|  | COC-1 | 100 | 100 | 100 | 80 |
| AVEFA | OC | 98 | 0 | 0 | 0 |
|  | COC-1 | 100 | 95 | 30 | 0 |
| PANTE | OC | 98 | 90 | 20 | 0 |
|  | COC-1 | 100 | 98 | 90 | 20 |
| SETVI | OC | 100 | 90 | 40 | 0 |
|  | COC-1 | 100 | 100 | 90 | 50 |
| SETLU | OC | 98 | 95 | 50 | 10 |
|  | COC-1 | 100 | 95 | 85 | 30 |

TABLE VI-continued

Effect of Oil Concentrate on Efficacy of Sethoxydim Across Species[1]

| SPECIES | Oil Concentrate[2] | Sethoxydim Rate (g/ha) | | | |
|---|---|---|---|---|---|
| | | 7.0 | 3.5 | 1.7 | 0.8 |
| SORHA | OC | 90 | 70 | 20 | 10 |
| | COC-1 | 100 | 100 | 98 | 60 |
| ECHCG | OC | 100 | 100 | 90 | 10 |
| | COC-1 | 100 | 100 | 100 | 60 |
| ZEAMX | OC | 50 | 20 | 0 | 0 |
| | COC-1 | 100 | 100 | 50 | 20 |

[1] Greenhouse trials with exposure to direct sunlight
[2] OC applied at 2.3 l/ha, COC-1 applied at 4.6 l/ha.

In Table VII, the greater efficacy of the crop oil concentrate of the subject invention in controlling ECHCG (echinochloa crus-galli) is demonstrated. The data indicates that cycloxydim at 50 g/ha has greater efficacy when used with the subject invention crop oil concentrate at 0.5 l/ha than cycloxydim at 75 g/ha with the "standard" concentrate at 1.5 l/ha. It even outperforms cycloxydim at 50 g/ha when used in conjunction with 5.0 kg/ha of ammonium sulfate and the "standard" concentrate at 1.5 l/ha, which is often the treatment of choice to enhance efficacy of certain herbicides systems.

TABLE VII

Echinochloa Crus-galli Control Using Cycloxydim

| Cycloxydim Rate, g/ha | OC[1] | COC-1[2] |
|---|---|---|
| 50 | 93 | 98 |
| 75 | 96 | 99 |
| 50 + ammonium sulfate @ 5.0 Kg/ha | 97 | |

[1] @1.5 l/ha
[2] 0.5 l/ha

Table VIII below shows the effect of using the crop oil concentrate of the subject invention to aid in control of AVEFA and LOLMU in barley with three different cyclohexenone herbicides. In all cases, the degree of control is much higher with the crop oil concentrate of the subject invention than with the "standard" concentrate.

TABLE VIII

Weed Control in Barley

| Herbicide @ rate | Concentrate* | Species: | | |
|---|---|---|---|---|
| | | LOLMU | AVEFA | OVERALL |
| Cyclohexenone | OC | 68 | 65 | 67 |
| B @ 200 g/ha | COC-2 | 87 | 95 | 94 |
| Cyclohexenone | OC | 58 | 58 | 58 |
| C @ 100 g/ha | COC-2 | 78 | 88 | 83 |
| Cyclohexenone | OC | 47 | 50 | 48 |
| D @ 50 g/ha | COC-2 | 79 | 94 | 86 |

*2 l/ha

Table IX demonstrates the improvement made possible by the crop oil concentrates of the subject invention when used for weed control in peas.

TABLE IX

Sethoxydim* Weed Control in Peas

| Concentrate** | Species: | | | | OVERALL |
|---|---|---|---|---|---|
| | TRZAX | AVESA | LOLMU | HORVU | |
| OC | 30 | 92 | 86 | 30 | 62 |
| COC-1 | 73 | 99 | 98 | 68 | 85 |
| COC-2 | 75 | 99 | 98 | 77 | 87 |

*at 150 g/ha
**at 2 l/ha

In Table X below is demonstrated the effect of the crop oil concentrates of the subject invention when compared to the common, locally used concentrate, LOC, in the control of SORHA (sorghum halepense) with two cyclohexenone herbicides.

TABLE X

Cyclohexenone Control of Sorghum halepense

| Herbicide @ Rate | Concentrate @ Rate | % Control |
|---|---|---|
| Sethoxydim @ 370 g/ha | LOC @ 2 l/ha | 60 |
| | COC-1 @ 2 l/ha | 89 |
| | COC-1 @ 1.5 l/ha | 82 |
| Cycloxydim @ 200 g/ha | LOC @ 2 l/ha | 60 |
| | COC-1 @ 2 l/ha | 89 |
| | COC-1 @ 1.5 l/ha | 89 |

Tables XI-XIV demonstrate that the subject invention crop oil concentrates are effective with a wide variety of herbicides. The herbicidal efficacy was evaluated in Greenhouse trials with a predetermined optimum amount of oil concentrate. The weed species tested reflect real conditions as would be found in relevant crops.

TABLE XI

EFFICACY OF CROP OIL CONCENTRATES IN VARIOUS HERBICIDES

| Herbicide | Oil Concentrate | Species: | | | | | | | | | | |
|---|---|---|---|---|---|---|---|---|---|---|---|---|
| | | AVEFA | BRAPP | CHEAL | DAOTE | DATST | DIGSA | ECHCG | IPOLA | SETVI | SORHA | ZEAMX |
| haloxyfop-methyl @ 31 g/ha | OC @ 2.3 l/ha | 0 | — | — | — | — | 40 | 50 | — | — | — | 50 |
| | COC-1 @ 4.6 l/ha | 30 | — | — | — | — | 90 | 100 | — | — | — | 100 |
| fluazifop-P—butyl @ 25 g/ha | OC @ 2.3 l/ha | — | 90 | — | — | — | 40 | 40 | — | — | 50 | 96 |
| | COC-1 @ 4.6 l/ha | — | 98 | — | — | — | 80 | 85 | — | — | 98 | 99 |
| paraquat @ 140 g/ha | X-77[1] @ 0.5 l/ha | 85 | — | — | — | — | — | — | — | — | — | — |
| | COC-1 @ 2.3 | 100 | — | — | — | — | — | — | — | — | — | — |

TABLE XI-continued

EFFICACY OF CROP OIL CONCENTRATES IN VARIOUS HERBICIDES

| Herbicide | Oil Concentrate | Species: AVEFA | BRAPP | CHEAL | DAOTE | DATST | DIGSA | ECHCG | IPOLA | SETVI | SORHA | ZEAMX |
|---|---|---|---|---|---|---|---|---|---|---|---|---|
| @ 9 g/ha | X-77 @ 0.5 l/ha | — | — | — | — | — | — | — | — | 45 | — | — |
|  | COC-1 @ 2.3 l/ha | — | — | — | — | — | — | — | — | 65 | — | — |
| acifluorfen |  |  |  |  |  |  |  |  |  |  |  |  |
| @ 18 g/ha | OC @ 2.3 l/ha | — | — | 15 | 25 | 90 | — | — | 40 | — | — | — |
|  | COC-1 @ 2.3 l/ha | — | — | 85 | 78 | 100 | — | — | 93 | — | — | — |
| @ 9 g/ha | OC @ 2.3 l/ha | — | — | 10 | 15 | 37 | — | — | 18 | — | — | — |
|  | COC-1 @ 2.3 l/ha | — | — | 90 | 75 | 98 | — | — | 23 | — | — | — |
| @ 4.5 g/ha | OC @ 2.3 l/ha | — | — | 5 | 5 | 12 | — | — | 10 | — | — | — |
|  | COC-1 @ 2.3 l/ha | — | — | 80 | 38 | 20 | — | — | 10 | — | — | — |

[1]X-77 is a product of the Chevron Chemical Co., San Francisco, CA.

TABLE XII

Efficacy of Postemergence Broadleaf Herbicides in Presence of Oil Concentrates

| Herbicide @ rate | Concentrate* | Species: DAOTE | XANPE |
|---|---|---|---|
| bentazon @ 1.12 kg/ha | OC | 62 |  |
|  | COC-1 | 78 |  |
| acifluorfen @ 36 g/ha | OC |  | 77 |
|  | COC-1 |  | 98 |
| acifluorfen @ 40 g/ha + bentazon @ 1.12 kg/ha | OC | 73 |  |
|  | COC-1 | 98 |  |

*at 2.3 l/ha

Table XIII and XIV show data from field trials indicating the superiority of oil concentrate of subject invention compared to "standard" concentrate.

TABLE XIII

Effect of Crop Oil Concentrates on Clumpcorn Control with Various Herbicides

| Herbicide @ rate | Concentrate @ 2.3 l/ha | ZEAMX[1]: 8-12" | 12+" |
|---|---|---|---|
| sethoxydim @ 168 g/ha | OC | 23 | 25 |
| 168 g/ha | COC-2 | 60 | 70 |
| fluazifop-P-butyl @ | OC | 78 | 80 |
| 210 g/ha | COC-2 | 88 | 85 |
| Fluazifop-P-butyl @ | OC | 60 | 65 |
| 100 g/ha | COC-2 | 68 | 68 |
| Fenoxaprop-ethyl @ | OC | 25 | 27 |
| 112 g/ha | COC-2 | 60 | 70 |

[1]Zea mays clumpcorn of 8-12 and 12+ inches height

TABLE XIV

Effect of Crop Oil Concentrates on Clethodim[1] Control of Various Weed Species

| Concentrate | Species: FESAR | BROSE | POAPR | AVESA | OVERALL |
|---|---|---|---|---|---|
| OC @ 2 l/ha | 90 | 58 | 92 | 93 | 81 |
| COC-2 2 l/ha | 94 | 84 | 92 | 95 | 90 |

[1]Clethodim @ 75 g/ha

The embodiments of the invention in which an exclusive privilege or property is claimed are defined as follows:

1. A crop oil concentrate, comprising
   (a) from about 20 to about 90 weight percent of a lower alkanol ester of a fatty acid; containing from 4-22 carbon atoms.
   (b) from about 4 to about 40 weight percent of an anionic surfactant selected from the group consisting of the partial sulfate and phosphate esters and carboxylates of monohydroxylfunctional polyoxyalkylene ethers, and
   (c) from 2 to about 20 weight percent of a long chain carboxylic acid containing from about 10 to about 20 carbon atoms.

2. The crop oil concentrate of claim 1 further comprising up to about 140 weight percent based upon the total weight of components (a), (b), (c), of
   (d) a hydrocarbon component.

3. The crop oil concentrate of claim 2 wherein said lower alkanol ester of a fatty acid is derived from a lower alkanol having from 1-4 carbon atoms, and wherein said fatty acid has from 10 to about 20 carbon atoms.

4. The crop oil concentrate of claim 3 wherein said lower alkanol ester of a fatty acid is selected from the group consisting of methyl laurate, methyl myristate, methyl stearate, methyl linoleate, methyl linolenate, methyl oleate, methyl palmitate, and mixtures thereof.

5. The crop oil concentrate of claim 2 wherein said partial sulfate esters, phosphate esters, and carboxylates are selected from the group consisting of the partial sulfate esters, phosphate esters, and carboxylates of a cogeneric mixture of monohydroxyl-functional polyoxyalkylene ethers having an average molecular weight of from about 400 to about 3000 Daltons.

6. The crop oil concentrate of claim 5 wherein said polyoxyalkylene ether has an average molecular weight of from 600 to about 1200 Daltons, and is prepared by oxyalkylating an aliphatic alcohol having from 10 to about 20 carbon atoms in the aliphatic residue.

7. The crop oil concentrate of claim 4 wherein said polyoxyalkylene ether has an average molecular weight of from 600 to about 1200 Daltons, and is prepared by oxyalkylating an aliphatic alcohol having from 10 to about 20 carbon atoms in the aliphatic residue.

8. The crop oil concentrate of claim 2 wherein said hydrocarbon component comprises a mixture of predominately aromatic hydrocarbons and up to about 30 percent by weight based upon the weight of the hydrocarbon component of a solvent soluble alcohol having from 5 to about 18 carbon atoms.

9. The crop oil concentrate of claim 8 wherein said hydrocarbon component comprises one or more alkylated aromatic hydrocarbons.

10. The crop oil concentrate of claim 8 wherein said solvent soluble alcohol is isooctanol.

11. A crop oil concentrate, comprising
(a) from about 30 to about 80 weight percent of a lower alkanol ester of a fatty acid containing from 10 to about 20 carbon atoms;
(b) from 4 to about 20 percent of an anionic surfactant selected from the group consisting of the partial sulfate and phosphate esters and carboxylates of monohydroxyl-functional polyoxyalkylene ethers having an average molecular weight of from about 600 to about 1200 Daltons; and
(c) from 4 to about 16 weight percent of a long chain carboxylic acid having from 10 to about 20 carbon atoms.

12. The crop oil concentrate of claim 11 further comprising from about 80 to about 120 weight percent based upon the total weight of components (a), (b) and (c) of (d) a hydrocarbon component.

13. The crop oil concentrate of claim 12 wherein said lower alkanol ester is selected from the group consisting of methyl laurate, methyl myristate, methyl stearate, methyl linoleate, methyl linolenate, methyl oleate, methyl palmitate, and mixtures thereof.

14. The crop oil concentrate of claim 12 wherein said lower alkanol ester comprises the methyl esters of one or more fatty acids derived from natural sources.

15. The crop oil concentrate of claim 12 wherein said long chain carboxylic acid is an unsaturated fatty acid.

16. The crop oil concentrate of claim 13 wherein said long chain carboxylic acid is oleic acid.

17. The crop oil concentrate of claim 14 wherein said long chain carboxylic is oleic acid.

18. The crop oil concentrate of claim 12 wherein said anionic surfactant is the partial phosphate ester of a monohydroxyl-functional polyoxyalkylene ether having a molecular weight of from about 600 to about 1200 Daltons.

19. The crop oil concentrate of claim 13 wherein said anionic surfactant is the partial phosphate ester of a monohydroxyl-functional polyoxyalkylene ether having a molecular weight of from about 600 to about 1200 Daltons.

20. The crop oil concentrate of claim 14 wherein said anionic surfactant is the partial phosphate ester of a monohydroxyl-functional polyoxyalkylene ether having a molecular weight of from about 600 to about 1200 Daltons.

21. The crop oil concentrate of claim 15 wherein said anionic surfactant is the partial phosphate ester of a monohydroxyl-functional polyoxyalkylene ether having a molecular weight of from about 600 to about 1200 Daltons.

22. The crop oil concentrate of claim 16 wherein said anionic surfactant is the partial phosphate ester of a monohydroxyl-functional polyoxyalkylene ether having a molecular weight of from about 600 to about 1200 Daltons.

23. The crop oil concentrate of claim 17 wherein said anionic surfactant is the partial phosphate ester of a monohydroxyl-functional polyoxyalkylene ether having a molecular weight of from about 600 to about 1200 Daltons.

24. The crop oil concentrate of claim 12 wherein said hydrocarbon component (d) comprises one or more aromatic hydrocarbons, and up to about 30 weight percent based on the total weight of (d), of a solvent soluble alcohol.

25. The crop oil concentrate of claim 16 wherein said hydrocarbon component (d) comprises one or more aromatic hydrocarbons and up to 30 weight percent based upon the total weight of (d), of a solvent soluble alcohol.

26. The crop oil concentrate of claim 24 wherein said hydrocarbon solvent soluble alcohol is present in an amount of from about 10 to about 20 percent by weight.

27. The crop oil concentrate of claim 26 wherein said alcohol is isooctanol.

28. The crop oil concentrate of claim 25 wherein said solvent soluble alcohol is present in an amount of from about 10 to about 20 percent by weight.

29. The crop oil concentrate of claim 28 wherein said alcohol is isooctanol.

30. A crop oil concentrate, comprising
(a) from about 35 to about 40 weight percent of a mixture which comprises the methyl esters of palmitic and oleic acids;
(b) from about 6 to about 9 weight percent of an anionic surfactant which is a mixture of the partial phosphate esters of a hydroxylfunctional polyoxyalkylene ether initiated with a $C_{10}$–$C_{14}$ aliphatic alcohol:
(c) from about 3 to about 7 weight percent of an unsaturated long chain carboxylic acid selected from the group consisting of oleic acid, linoleic acid, and linolenic acid; and
(d) from 40 to about 60 weight percent of a hydrocarbon component further comprising based on the weight of the hydrocarbon component, up to about 10 percent of a solvent soluble alcohol having from 5 to about 10 carbon atoms.

31. The crop oil concentrate of claim 1 wherein said long chain carboxylic acid (c) is derived at least in part through the in situ hydrolysis of component (a).

32. The crop oil concentrate of claim 2 wherein said long chain carboxylic acid (c) is derived at least in part through the in situ hydrolysis of component (a).

33. The crop oil concentrate of claim 11 wherein said long chain carboxylic acid (c) is derived at least in part through the in situ hydrolysis of component (a).

34. The crop oil concentrate of claim 30 wherein said long chain carboxylic acid (c) is derived at least in part through the in situ hydrolysis of component (a).

* * * * *